United States Patent
Yang et al.

(10) Patent No.: US 9,011,648 B2
(45) Date of Patent: Apr. 21, 2015

(54) CONVERSION OF CARBON DIOXIDE INTO USEFUL ORGANIC PRODUCTS BY USING PLASMA TECHNOLOGY

(71) Applicant: National Tsing Hua University, Hsinchu (TW)

(72) Inventors: Arnold Chang-Mou Yang, Hsinchu (TW); Yi-Hsin Chang, Hsinchu (TW); Chun-Chih Chang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 137 days.

(21) Appl. No.: 13/749,075

(22) Filed: Jan. 24, 2013

(65) Prior Publication Data

US 2013/0264187 A1 Oct. 10, 2013

Related U.S. Application Data

(63) Continuation-in-part of application No. 12/213,764, filed on Jun. 24, 2008, now abandoned.

(30) Foreign Application Priority Data

Feb. 4, 2008 (TW) .............................. 97104132 A

(51) Int. Cl.
*B01J 19/08* (2006.01)
*B01J 19/12* (2006.01)
(Continued)

(52) U.S. Cl.
CPC .............. *B01J 19/087* (2013.01); *B01J 19/126* (2013.01); *B01J 19/129* (2013.01); *Y02C 10/04* (2013.01); *B01J 19/088* (2013.01); *B01D 53/32* (2013.01); *B01D 53/62* (2013.01); *B01D 2257/504* (2013.01); *B01D 2258/01* (2013.01); *B01D 2259/818* (2013.01); *B01J 2219/0809* (2013.01); *B01J 2219/083* (2013.01); (Continued)

(58) Field of Classification Search
CPC ........ B01J 19/08; B01J 19/088; B01J 19/129; B01J 19/126; B01J 2219/0835; B01J 2219/0869; B01J 2219/0809; B01J 2219/083; B01J 2219/0875; C10G 2/40; C10G 2/50; C10G 2400/04; C10G 2400/02; C10G 2300/4012; C07C 27/04; B01D 53/62; B01D 53/32; B01D 2258/0283; B01D 53/92; B01D 2251/208; B01D 2259/818; B01D 2258/01; B01D 2257/504; Y02C 10/04
USPC ......................................................... 204/164
See application file for complete search history.

(56) References Cited

U.S. PATENT DOCUMENTS

2006/0113181 A1* 6/2006 Hirata et al. ................... 204/173

OTHER PUBLICATIONS

Ihara et al., "Plasma Reduction of CO2 with H2O for the Formation of Organic Compounds", Bull. Chem. Soc. Jpn, 467, 312-314 (1994).*

(Continued)

*Primary Examiner* — Kishor Mayekar
(74) *Attorney, Agent, or Firm* — Hannah M. Tien

(57) ABSTRACT

The present invention relates to a method of conversion of carbon dioxide into organic products using plasma technology comprising the steps of (a) providing a reaction chamber; (b) introducing a counterpart molecule and carbon dioxide into the reaction chamber; (c) initiating a plasma in the reaction chamber; and (d) converting the carbon dioxide into organic products, wherein the organic products do not contain formic acid and formaldehyde, and wherein the counterpart molecule consists of water molecule.

14 Claims, 18 Drawing Sheets

(51) Int. Cl.
*B01D 53/32* (2006.01)
*B01D 53/62* (2006.01)
*C07C 27/04* (2006.01)
*C10G 2/00* (2006.01)
*B01D 53/92* (2006.01)

(52) U.S. Cl.
CPC .. *B01J 2219/0835* (2013.01); *B01J 2219/0869* (2013.01); *B01J 2219/0875* (2013.01); *C07C 27/04* (2013.01); *B01D 53/92* (2013.01); *B01D 2251/208* (2013.01); *B01D 2258/0283* (2013.01); *C10G 2/40* (2013.01); *C10G 2/50* (2013.01); *C10G 2300/4012* (2013.01); *C10G 2400/02* (2013.01); *C10G 2400/04* (2013.01)

(56) References Cited

OTHER PUBLICATIONS

Ihara et al. ("Formation of Methanol by Microwave-Plasma Reduction of CO2 with H2O", Bull. Chem. Soc. Jpn, 69, 241-244 (1996).*
Liu ("Non-thermal plasma approaches in CO2 utilization", Fuel Processing Technology 58, 119-134 (1999).*

\* cited by examiner

| Monomer | C/O | Binding types (%) | | | | |
| --- | --- | --- | --- | --- | --- | --- |
| | | C=C | C-H, C-C | C-O | C=O | COOH, COOR |
| Ethyl naphthalene | 3.8 | 13.6 | 56.0 | 17.0 | 7.2 | 6.2 |
| Toluene | 6 | 11.3 | 71.6 | 12.5 | 1.8 | 2.8 |
| Decadiene | 16 | 2.9 | 86.6 | 8.1 | 1.6 | 0.8 |

| Monomer | C/O | Binding types (%) | | | | |
|---|---|---|---|---|---|---|
| | | C=C | C-H, C-C | C-O | C=O | COOH, COOR |
| Gasoline | 7.0 | 9 | 76 | 9 | 2 | 4 |
| Diesel | 5.6 | 6 | 80 | 9 | 2 | 3 |
| Kerosene | 6.5 | 12 | 74 | 9 | 2 | 4 |

CONVERSION OF CARBON DIOXIDE INTO USEFUL ORGANIC PRODUCTS BY USING PLASMA TECHNOLOGY

CROSS REFERENCE TO RELATED APPLICATIONS

This application is a Continuation-In-Part of U.S. patent application Ser. No. 12/213,764 filed on Jun. 24, 2008, now pending, and is hereby incorporated by reference in its entirety. Although incorporated by reference in its entirety, no arguments or disclaimers made in the parent application apply to this divisional application. Any disclaimer that may have occurred during the prosecution of the above-referenced application(s) is hereby expressly rescinded. Consequently, the Patent Office is asked to review the new set of claims in view of all of the prior arts of record and any search that the Office deems appropriate.

FIELD OF THE INVENTION

The present invention relates to a method for conversion of carbon dioxide into useful organic products, it more specifically relates to a method using plasma technology to convert carbon dioxide with other molecules into useful organic products.

BACKGROUND OF THE INVENTION

In the last few decades, the rapid growth in world population and industrial development has lead to massively increased usage of fossil fuels such as coal, petroleum and natural gas and the resulting formation of carbon dioxide; moreover, due to the deforestation and the reduction of rain forest, the dynamic equilibrium of carbon dioxide formation and conversion has been seriously destroyed. Consequently carbon dioxide content in the atmosphere increases year by year; the seriousness of global warming attributed to carbon dioxide emission has increased, and the potential dangers to humanity have driven many countries to research the reduction of carbon dioxide.

The reduction technology of carbon dioxide currently can be divided into two methods, physics-based and chemistry-based. For physics-based methods, carbon dioxide is captured from atmosphere and then stored underground or under the sea bed using high pressure compression. From the viewpoint of equilibrium and cycling of carbon dioxide on earth, the amount of carbon dioxide has not been reduced; hence, the use of chemistry-based methods to convert carbon dioxide into useful materials has become the core of carbon dioxide reduction technology. However, although several chemistry-based methods have been developed for the conversion of carbon dioxide, these chemical processes have the following limits: First, since carbon dioxide is very chemically inactive, catalysts must be used for conversion reactions, but catalysts are very expensive and the reaction lifetime is limited; Second, since carbon dioxide and its counterpart molecules are usually in different phases at room temperature and atmospheric pressure, the reaction must be carried out under high temperature and high pressure environments; Third, such long reaction times are required for the chemical reactions, that the reaction times can be several hours to several days depending on the types of catalysts; all the above mentioned issues have limited the massive demands for carbon dioxide conversion in industries. Moreover, such chemical processes are not suitable for household applications.

Based on these considerations, a plasma-based technology is presented for carbon dioxide conversions. When molecules enter into electric fields, they are excited and ionized by collision with accelerated electrons to generate various species such as atoms, electrons, ions, free radicals, etc. The mixture of these species is plasma. These activated species generated by plasma bombardments can recombine to form new products. The molecules used in this plasma processes do not have to contain chemically active groups, such as $C=C$ bonds. As compared to the complicated processes and steps in conventional chemical syntheses, the plasma process is simple and fast. Besides, no solvent needs to be used and the hazard to the environment is greatly reduced; moreover, mass production can be easily reached to satisfy economic efficiency in industries. Besides, since plasma can be initiated in a simple device, it can thus be miniaturized to apply in portable or mobile commercial products, which will be a great advantage for the plasma technology to be extended to more applications.

Some studies have been aimed at the reaction mechanism of carbon dioxide in plasma. Carbon dioxide consists of two strong covalent bonds with low chemical activity; the conventional synthesis of carbon dioxide has to be induced only using catalyst activation. Buser et al. (J. App. Phy. 41, 472, 1970) found that carbon dioxide in plasma can be decomposed into carbon monoxide through vibration excitation. It was reported that as carbon dioxide is decomposed via the anti-symmetrical stretching mechanism, the initial energy is 0.1 electron volt (eV) and the energy required to overcome the band gap is 5.5 eV. This energy is smaller than the direct dissociation energy of $C=O$ bond, which is about 8 eV. Therefore, via plasma activation, the bond dissociation of carbon dioxide can be achieved at a lower energy level, and the subsequent recombined reactions can be carried out. Besides, the past studies reported that the carbon dioxide can be converted into hydrophilic functional groups by plasma activation, such as carboxylic acid or alcohol, etc. When such derivative functional groups from carbon dioxide are attached to the material surface, hydrophilic properties of material surfaces can be enhanced.

SUMMARY OF THE INVENTION

The present invention relates to a method of conversion of carbon dioxide into organic products using plasma technology comprising the steps of: (a) providing a reaction chamber; (b) introducing a counterpart molecule and carbon dioxide into the reaction chamber; (c) initiating a plasma in the reaction chamber; and (d) converting the carbon dioxide into organic products, wherein the organic products do not contain formic acid and formaldehyde, and wherein the counterpart molecule consists of water molecule.

DETAILED DESCRIPTION OF THE INVENTION

In the invention, plasma technology is adopted to activate carbon dioxide with counterpart molecules in the reaction chamber and to perform chemical bond breaking and re-combination reactions. In the following, the related figures will be referred to for the description of better embodiment of the present invention, wherein the same component will be described by the same symbol.

Figure 1:
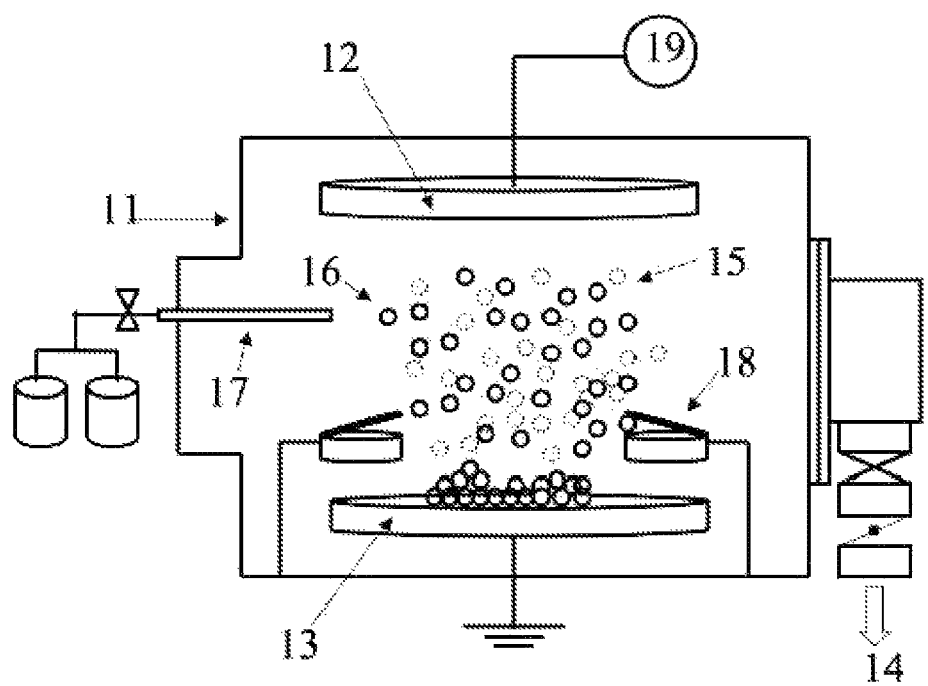
FIG. 1 is an illustration of the instrument used in the embodiment of the present invention using plasma technology to convert carbon dioxide into organic products.

For the steps of a better embodiment of the present invention, please refer to FIG. 1. FIG. 1 is the perspective view diagram of capacitively coupled plasma. First, carbon dioxide conversion reaction is conducted in reaction chamber 11. Reaction chamber 11 can be glass, metal or other alloy; in reaction chamber 11, it includes an upper electrode 12 and a lower electrode 13, which are used to generate plasma. Reaction chamber 11 can be pumped down to vacuum through vacuum ventilation end 14. Then we introduce carbon dioxide 15 and the counterpart molecule 16 into the reaction chamber 11; if counterpart molecule 16 is gas, it can be injected into reaction chamber 11 through injection end 17, or counterpart molecule 16 can be pushed into the reaction chamber 11 through carrier gas and through the injection end 17; if counterpart molecule 16 is liquid or solid, it can be vaporized by heating, vaporized with plasma assistance or vaporized in combination way in the source boat 18 of reaction chamber 11 and get mixed with carbon dioxide; or it can be vaporized by heating outside the reaction chamber 11, and then introduced through injection end 17 into the reaction chamber 11. Reactors using other types of plasma, such as inductive-coupled plasma and atmospheric-pressure plasma, are also readily compatible with this disclosed invention.

Next, the experimental parameters of better embodiment of the current invention are described.

First, counterpart molecule 16 can be solid, liquid or gas, it can also be inorganic, for example: water, it can also be organic; in the structure, it can be a compound that contains unsaturated bonds or a compound that contains entirely saturated bonds, they include: single ring or multiple rings compounds, for example: aromatic ring type, long-chain unsaturated hydrocarbon compounds or long-chain saturated hydrocarbon compounds, for example: alkene, alkyne hydrocarbons; or alkane hydrocarbons. We then introduce counterpart molecules 16 and carbon dioxide into the vacuum reaction chamber 11 with reaction chamber vacuum level of 0.01~760 torr. Next, we turn on the plasma to start the activation reaction, here the so-called plasma, according to the supply way, can be microwave plasma, RF plasma or DC plasma; or according to operation pressures, can be low pressure plasma, for example: capacitively coupled plasma or inductively coupled plasma, or atmosphere plasma, for example: electron beam discharge, corona discharge or dielectric discharge; the operation power of the plasma is in the range of 0.1~1000 W, or better controlled at 1~500 W or especially good at 10-300 W. Through the control of different plasma parameters, the counterpart molecule structures, and mixing proportions, products generated could be gas, liquid or solid, they can also be small molecules, oligomers and polymers, or it can be compounds with OH groups, carboxylic groups or ester groups.

From the products due to the embodiment of the technology of present invention, oligomers and small molecules can be used as fuel; polymers can be used as plastic products. Moreover, the current invention, depending on the design of the embodied device, can be applied in the portable device, for example: applied in exhaust pipes of automobiles or motorcycles, or can be applied in the fixed device, for example: in smokestacks of factories.

Therefore, the present invention provides a method of conversion of carbon dioxide into organic products using plasma technology comprising the steps of:
(a) providing a reaction chamber;
(b) introducing a counterpart molecule and carbon dioxide into the reaction chamber;
(c) initiating a plasma in the reaction chamber; and
(d) converting the carbon dioxide into organic products, wherein the organic products do not contain formic acid and formaldehyde,
and wherein the counterpart molecule consists of water molecule.

In a preferred embodiment, the water molecule is vaporized in the reaction chamber by heating, with plasma assistance or a combination of both.

In another preferred embodiment, the water molecule is vaporized outside the reaction chamber and the vapor is introduced into the reaction chamber directly.

In still another preferred embodiment, the water molecule is injected directly or introduced into the reaction chamber by carrier gas.

In a preferred embodiment, the reaction chamber is of glass, metallic materials, ceramics or polymers. Preferably, the chamber pressure is 0.01~760 torr.

In a preferred embodiment, the plasma is low pressure plasma or atmosphere plasma. Preferably, the low pressure plasma is capacitively coupled plasma or inductively coupled plasma; the atmosphere plasma is electron beam discharge, corona discharge or dielectric discharge.

In another preferred embodiment, the plasma is microwave plasma, radio frequency (RF) plasma or direct current (DC) plasma.

In a preferred embodiment, the power of the plasma is 0.1-1000 W.

In a preferred embodiment, the organic products formed by the reaction are polymers, oligomers or small molecules.

In a preferred embodiment, the organic products formed by the reaction are gas, liquid or solid.

In a preferred embodiment, the organic products formed by the reaction are compounds that contain OH groups, carboxylic groups or ester group.

In another preferred embodiment, the organic products formed by the reaction contain gasoline or diesel fuel.

In a preferred embodiment, the organic products are used in the fuel application.

In another preferred embodiment, the organic products are applied as plastic products.

In still another preferred embodiment, the organic products are used as industrial materials, such as materials for producing cosmetics, food, textiles, etc.

In a preferred embodiment, the above method is applied in portable device or fixed device. Preferably, the portable device is applied in exhaust pipes of automobiles or motorcycles; the fixed device is used in a factory smokestack or household chimney.

EXAMPLES

The preferred embodiments of the present invention will be described in detail below. The examples below are non-limiting and are merely representative of various aspects and features of the present invention.

Example 1

Figure 2:
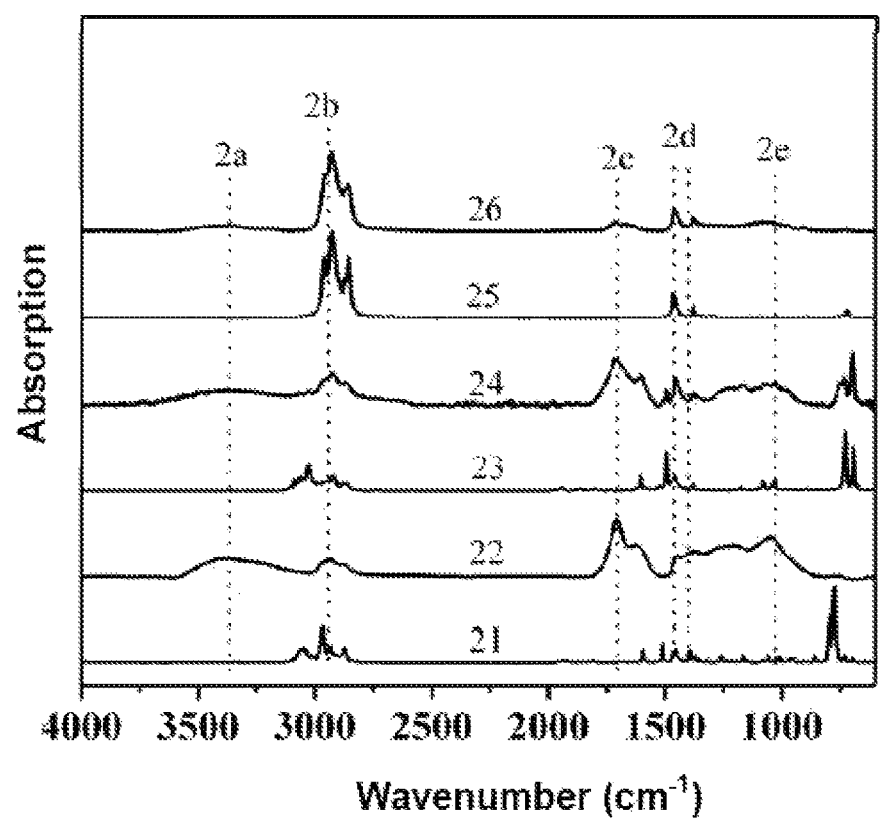
FIG. 2 shows the IR spectra of organic products obtained through plasma activation reaction of ethyl naphthalene, toluene and decadiene with carbon dioxide in the first embodiment of the present invention.
Figures 3A, 3B:
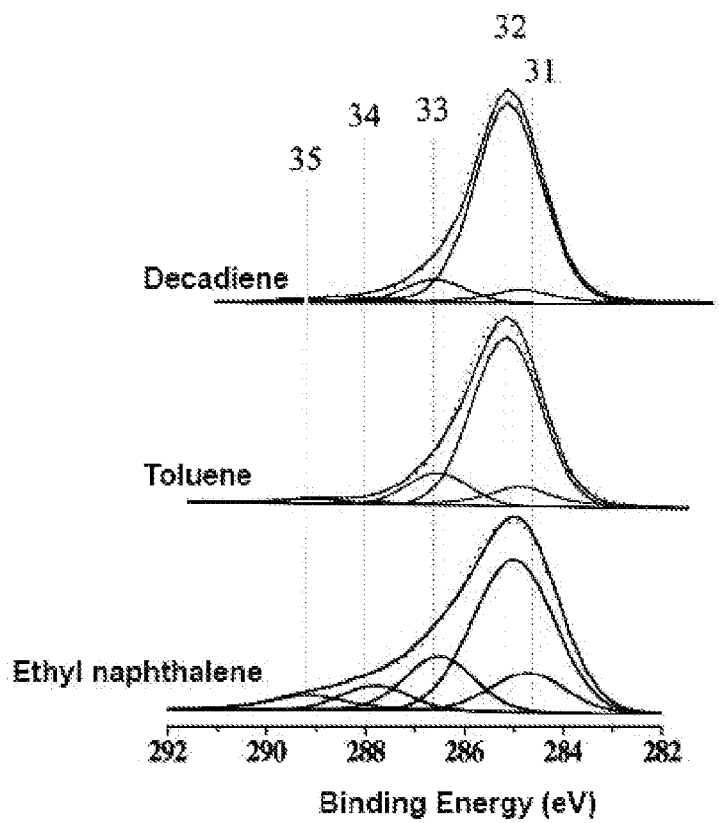
FIG. 3A shows the X-ray photoelectron C1s spectrum of organic products obtained through plasma activation reaction of ethyl naphthalene, toluene and decadiene with carbon dioxide in the first embodiment of the present invention.
FIG. 3B shows the curve-fitting results of the X-ray photoelectron C1s spectra of organic products obtained through plasma activation reaction of ethyl naphthalene, toluene and decaidene with carbon dioxide in the first embodiment of the present invention.

Direct Conversion of $CO_2$ with the Counter Molecules of Small Organic Molecules in an Inductive-Coupled Plasma Reactor In the first embodiment of the present invention, ethyl naphthalene was selected as the counterpart molecules, plasma power was controlled at 200 W, after a reaction time of 5 minutes, and the resulting product was polymer with molecular weight in the range of 60,000-100,000. The IR spectrum of this polymer product was as shown in curve 22 of FIG. 2, which proved that through the use of such plasma activation technology, carbon dioxide was indeed converted into products that contained carboxylic acid or OH group. When the plasma power was reduced to 10 W, then the resulting product was oligomers of low molecular weight with a viscous property. This proved that through the adjustment of plasma power, the molecular weight of the product converted from carbon dioxide was controlled. If the counterpart molecules were changed into toluene or decadiene, then the IR spectra of obtained polymer products were as shown in 24, 26 of FIG. 2, and it was seen that through the change of the structure of the counterpart molecules, carboxylic acid or OH groups was effectively connected to the products, but only somehow different in the amounts of these groups. Its quantitative functional groups was calculated from X-ray photoelectron C1s spectra as shown in FIG. 3A, and the curve fitting result was as shown in FIG. 3B. It was seen that when the counterpart molecules consisted of aromatic ring structures, more carbon dioxide derived functional groups was connected to the products, which included ether/alcohol groups (C—O), carbonyl group (C=O) and carboxylic group (COOR).

Example 2

Figure 4:
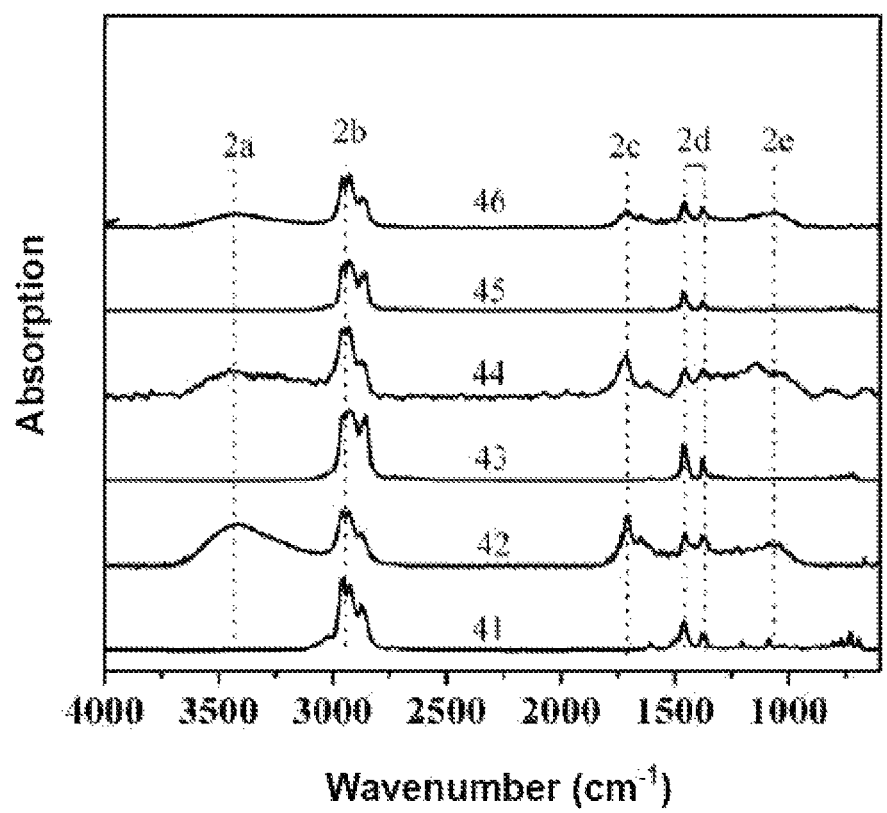
FIG. 4 shows the IR spectra of organic products obtained through plasma activation reaction of gasoline, kerosene, and diesel oil with carbon dioxide in the second embodiment of the present invention.
Figures 5A, 5B:
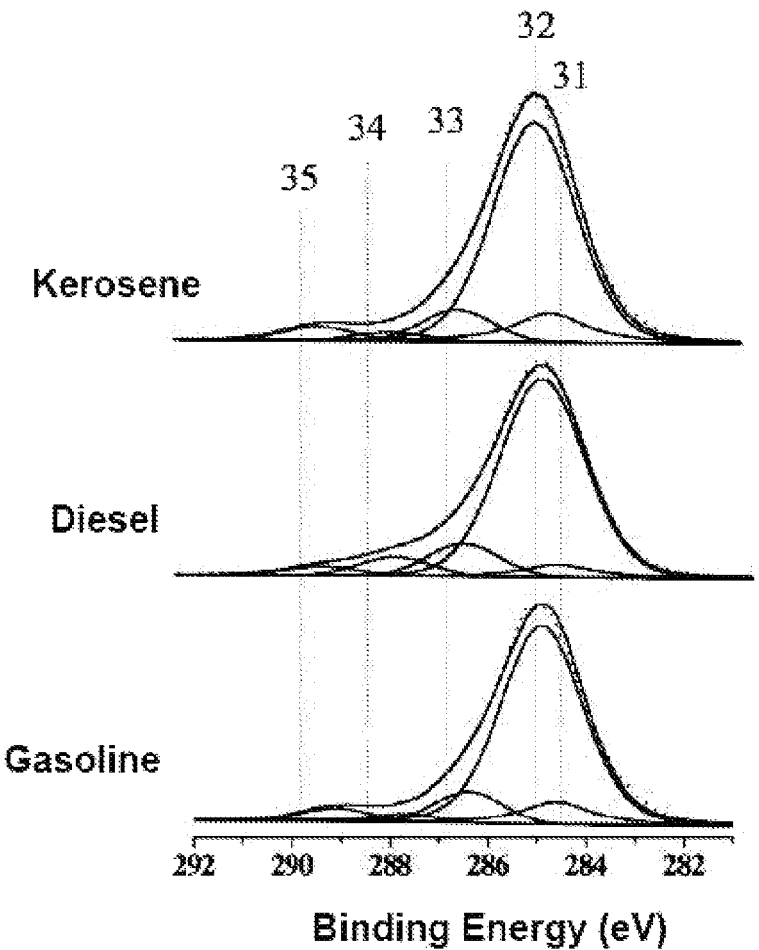
FIG. 5A shows the X-ray photoelectron C1s spectra of organic product obtained through plasma activation reaction of gasoline, kerosene, and diesel oil with carbon dioxide in the second embodiment of the present invention.
FIG. 5B shows the curve fitting results of the X-ray photoelectron C1s spectra of organic products obtained through plasma activation reaction of gasoline, kerosene, and diesel oil with carbon dioxide in the second embodiment of the present invention.

Direct Conversion of $CO_2$ with the Counter Molecules of Petroleum Fuel in an Inductive-Coupled Plasma Reactor In the second embodiment of the present invention, the counterpart molecules for carbon dioxide conversion reaction were petroleum fuel, which included gasoline, diesel oil and kerosene, etc.; the obtained products were different depending on the plasma powers and the mixing ratios between carbon dioxide and counterpart molecules, which were gas, liquid and solid compounds; the IR spectra were shown in FIG. 4, and the X-ray photoelectron spectra were shown in FIGS. 5A and 5B. When different structures of counterpart molecules were used, the carbon dioxide derived functional groups were observed on obtained products, including ether/alcohol groups (C—O), carbonyl group (C=O) and carboxylic group (COOR). Therefore, after petroleum fuel and carbon dioxide were activated by plasma, they co-reacted to form products that were mainly consisted of hydrocarbons containing OH group and COOR group. If these products were volatile compounds, it could then be used as fuel.

Example 3

Figure 6:
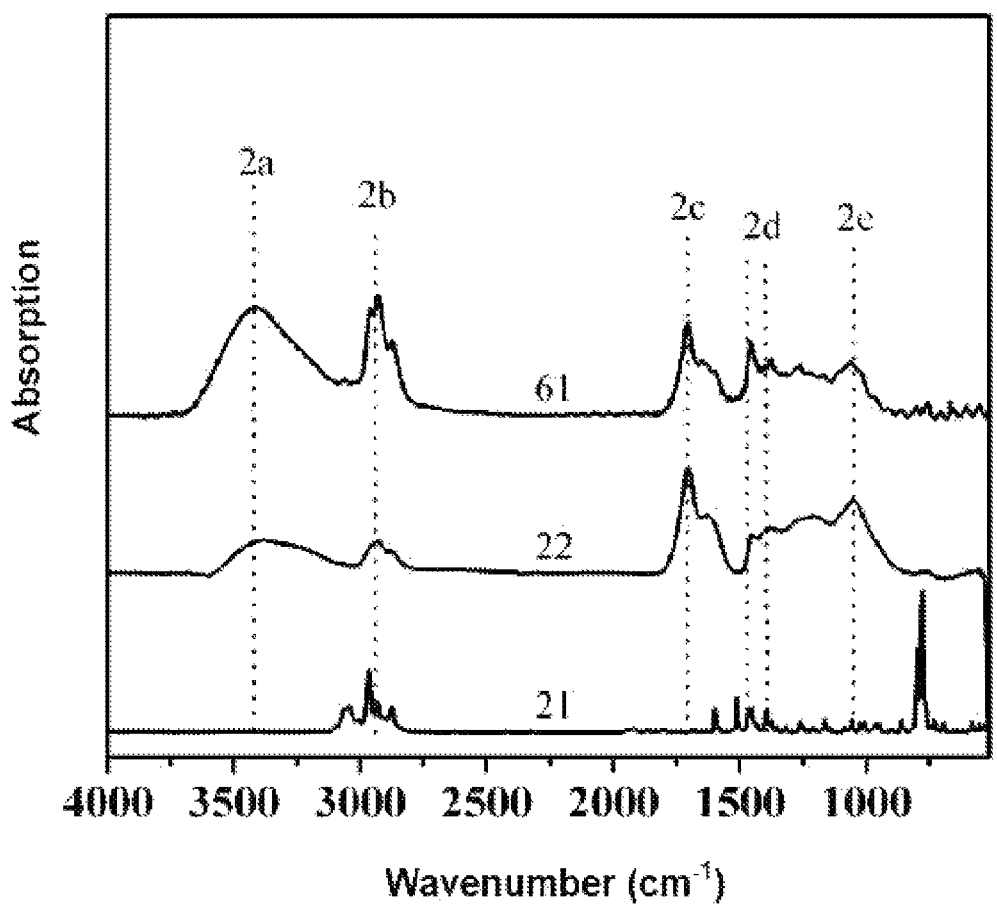
FIG. 6 shows the IR spectra of organic products obtained through plasma activation reaction of ethyl naphthalene and water with carbon dioxide in the third embodiment of the invention.

Direct Conversion of $CO_2$ with the Counter Molecules of Ethyl Naphthalene and Water in an Inductive-Coupled Plasma Reactor In the third embodiment of the present invention, ethyl naphthalene and water were selected as counterpart molecules, both monomers were vaporized and injected into the plasma reaction chamber with plasma power controlled at 200 W. After 5 minutes of reaction, the IR spectrum of the obtained product was as shown in curve 61 of FIG. 6; when compared to product that was not added with water molecule, the result was as in curve 22. According to the result, when water molecule was added into the co-reaction system of carbon dioxide and naphthalene, the intensity of OH absorption in the product increased obviously, which proved that the adding of water molecule was helpful to the generation of OH group in the product converted from carbon dioxide. Since the OH group was combustible functional groups, the products could thus be used as fuel.

Example 4

Direct Conversion of $CO_2$ and $H_2O$ to Fuels in Atmospheric Pressure Plasma Jet (APPJ)

In this embodiment of the present invention, water was selected as the counterpart molecule. The Experiment was conducted in an atmospheric Pressure Plasma Jet (APPJ) reactor powered by RF (13.56 MHz) at 45 W, 50 W, 55 W, 60 W (glow discharge), 65 W, 70 W (arc discharge). The voltage between two electrodes (glow discharge) is within the range of 400~700 Volts and the electrode gap is 1.3 mm. The reactants are $CO_2$ (3 SLM) and $H_2O$ (in the form of vapor supplied by water heated at 50, 60, 70, 80, 90 or 99° C.). The $CO_2$ gas injected into water tank and then the mixture of $CO_2$ and water vapor was introduced into APPJ reactor. The reaction time was 30 minutes per batch. The $H_2O/CO_2$ ratio was shown in Table 1:

TABLE 1

| $T_{tank}$ | 50° C. | 60° C. | 70° C. | 80° C. | 90° C. | 99° C. |
|---|---|---|---|---|---|---|
| $T_{APPJ}$ | 27.7° C. | 31.2° C. | 35.1° C. | 40.2° C. | 50.0° C. | 58.2° C. |
| Relative Humidity | 99% | 99% | 99% | 99% | 99% | 99% |
| $VD_{H2O}$ (g/m$^3$) | 26.62 | 32.23 | 39.56 | 51.02 | 79.89 | 112.01 |
| $n_{H2O}$ (mol/m$^3$) | 1.48 | 1.79 | 2.20 | 2.83 | 4.44 | 6.22 |
| $n_{CO2}$ (mol/m$^3$) | 39.07 | 38.31 | 37.39 | 36.11 | 33.31 | 30.60 |
| $H_2O/CO_2$ | 0.038 | 0.047 | 0.059 | 0.078 | 0.133 | 0.203 |

Figure 7A:
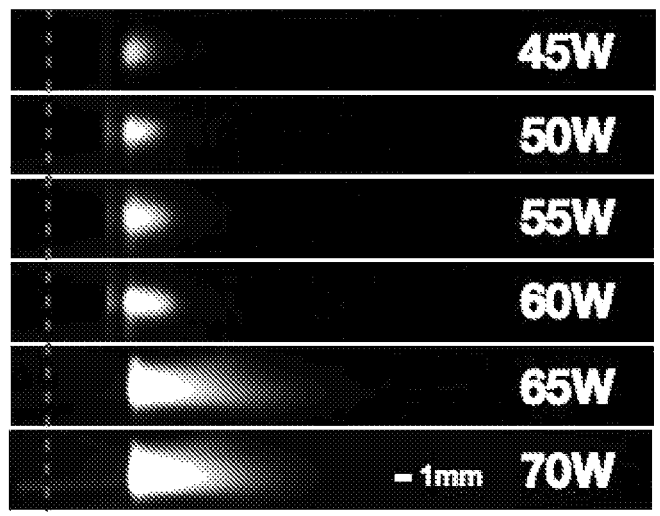
FIG. 7A shows the side-view CCD images of the $CO_2/H_2O$ APPJ from 45 to 70 W (The dot line represents the position of the tip of the inner electrode).
Figure 7B:
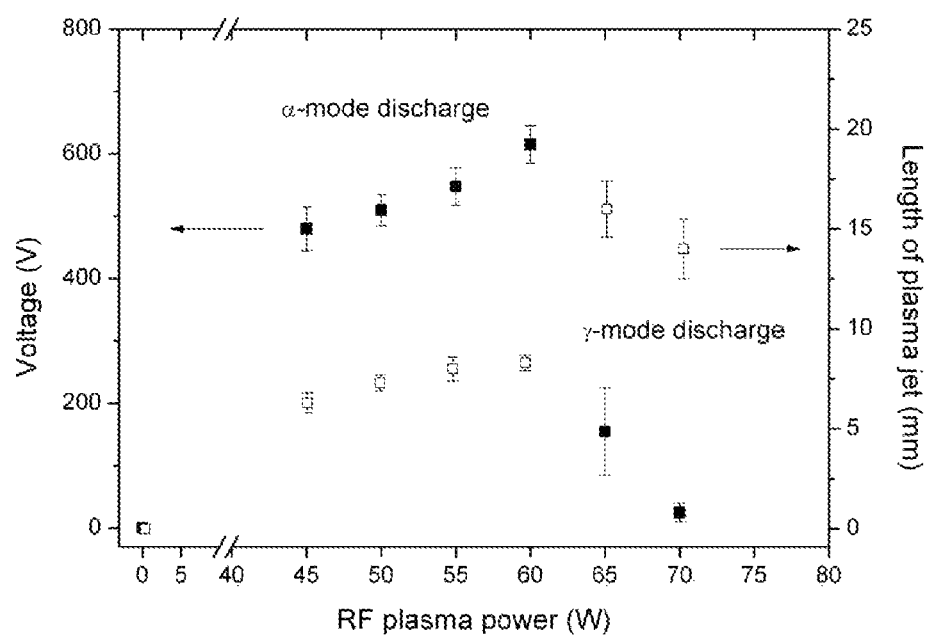
FIG. 7B shows the electrode voltage and length of plasma jet as a function of RF plasma powers as it relates to the generation of two types of electrical discharge under CO2/H2O APPJ. The condition of FIGS. 7A and 7B is as follows: $CO_2$: 3SLM; $H_2O/CO_2$=0.078.

The discharge in $CO_2/H_2O$ atmospheric pressure plasma jet was shown in FIG. 7. The α mode discharge was sustained by bulk ionization that the electrons are oscillated with the draft amplitude and are trapped in the bulk plasma region. At higher RF powers, the breakdown of the α sheath took place and a so-called gamma (γ) mode occurs. The γ mode discharge was sustained by secondary electron emission from the electrodes similar to the direct-current (DC) discharge case. The minimum sparking potential for $CO_2$ and $H_2O$ were higher than that of inert gas, much more voltage was needed for igniting a mode discharge. On the other hand, the applied high voltages would result in the direct ignition of γ mode discharge in $CO_2/H_2O$ and $CO_2$ atmospheric pressure plasma jets. The main mechanism of the discharge instability was the sheath breakdown that eventually leads to the thermal instability.

Figure 8A:
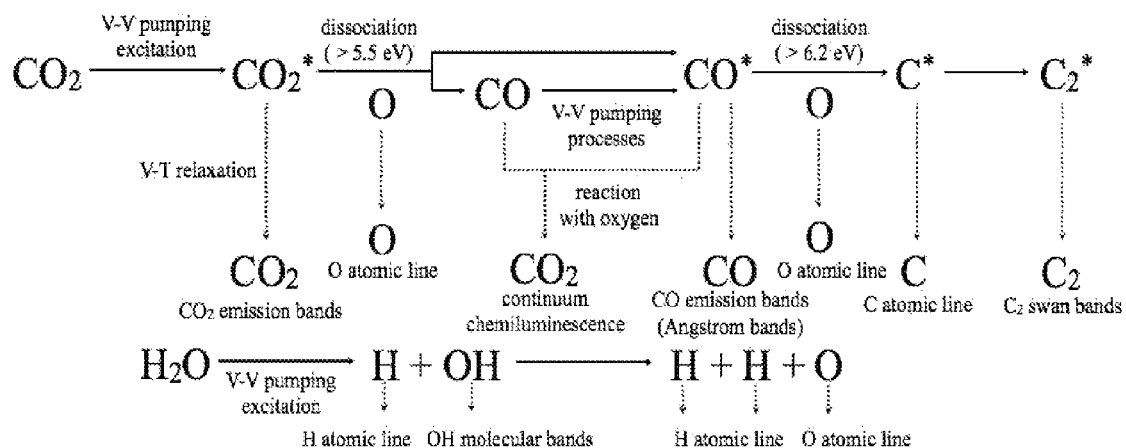
FIGS. 8A-8C show the reaction in $CO_2/H_2O$ atmospheric pressure plasma jet by optical emission spectroscopy (OES). The condition of FIGS. 8A-8C is as follows: $CO_2$: 3SLM; $H_2O/CO_2$=0.078.
Figure 8B:
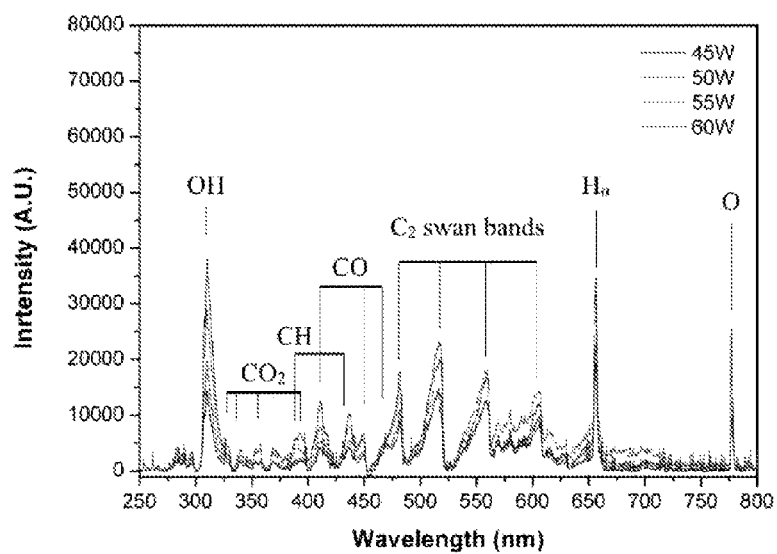
Figure 8C:
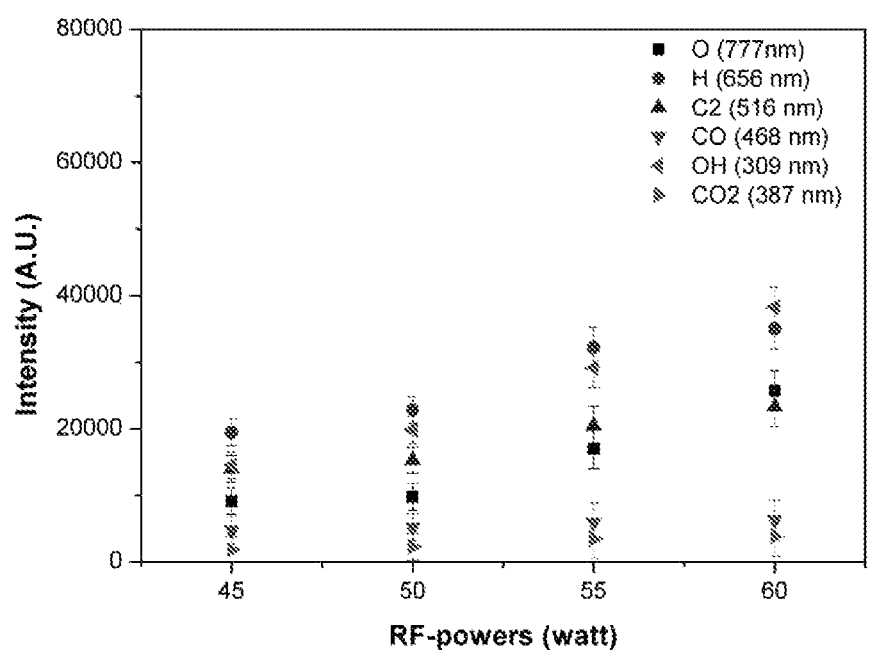

The conversion reaction was monitored by detecting the discharge emission using the Optical Emission Spectrometer (OES, B&W BRC111A spectrometer with the slit of 5 nm from 250 to 800 nm) via an optical fiber located at 30 mm from the APPJ nozzle and viewed in an axial direction. Furthermore, for products collection, all products flowed through a cooling channel (Graham condenser fixed at 4° C., controlled and circulated by a chiller; channel length=15 cm). The liquid products were condensed and collected by a two-neck bottle while the gaseous products were collected by a gas tank (volume=1 liter). The gas tank is filled with helium gas first and then the gaseous products flow into gas tank for 30 minutes. The reaction in $CO_2/H_2O$ atmospheric pressure plasma jet by OES method was shown in FIG. 8B. Clearly, from the OES spectra, the formation of organic compounds was detected as illustrated by the Oxygen atomic lines, CO molecular bands, $CO_2$ molecular bands, H atomic lines, OH molecular bands, and the $CH_2$ molecular bands, in addition to the heat continuum. The reactions in the plasma reactor were expected to follow the reaction route based on the consideration of the molecular bond strengths, as shown in FIG. 8A. The dependence of these molecular species in the plasma reactions as a function of the RF power was shown in FIG. 8C.

The products were analyzed by a gas chromatographer (GC) coupled with a differential pumped quadruple mass spectrometer (MS, Hewlett-Packard Micromass TRIO-2000, in NCTU). A capillary column (SGE BP-21, FFAP) was utilized with helium as carrier gas. For liquid samples, injector temperature was set at 250° C., column temperature programmed from 30 to 250° C. (30 to 80° C., linear heating rate 2° C.·min-1; 80 to 250° C., linear heating rate 20° C.·min-1; and finally held at 250° C. for 5 min) while for gaseous sample the injector temperature was at 30° C., column temperature fixed at 30° C. Mass spectra were recorded in full-scan mode in the m/z range 31 to 200 amu at the standard ionizing electron energy of 30 eV. The mass spectra were matched by means of available libraries and the species were identified through the interpretation of their mass spectra according to the typical fragmentations pattern of oxygenate compounds.

Figure 9A:
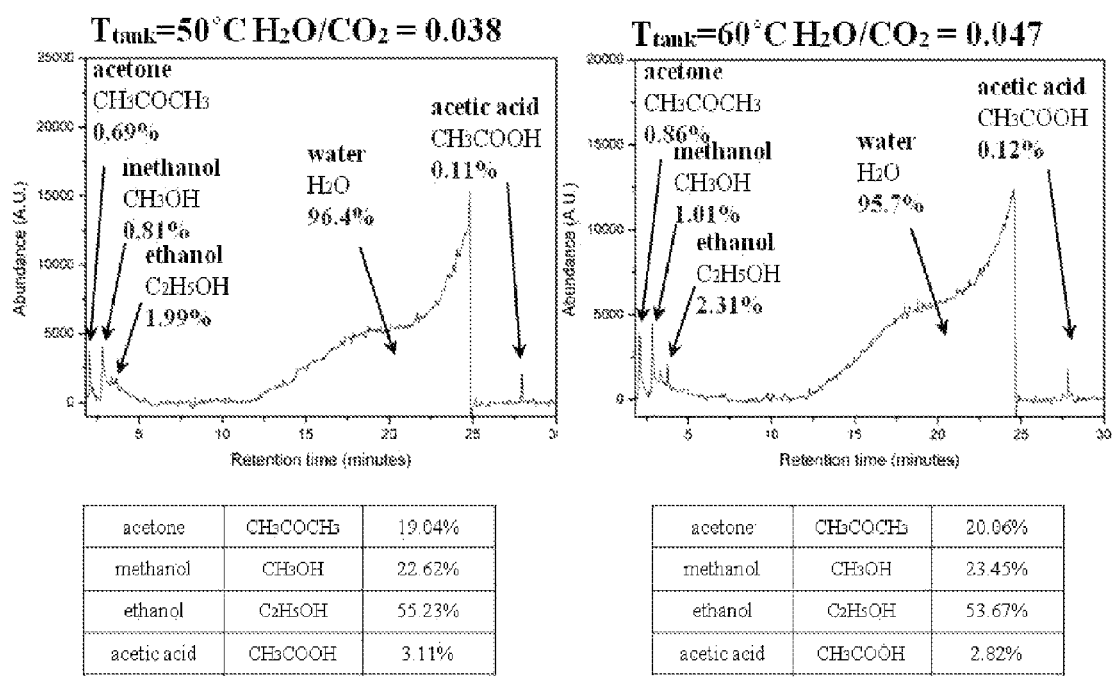
FIGS. 9A-9E shows the GC-MS results with different $H_2O/CO_2$ ratio revealing the concentration and selectivity of the produced compounds in the collected liquid products. The condition of FIGS. 9A-9E is as follows: plasma power: 60 W; $CO_2$: 3SLM.
Figure 9B:
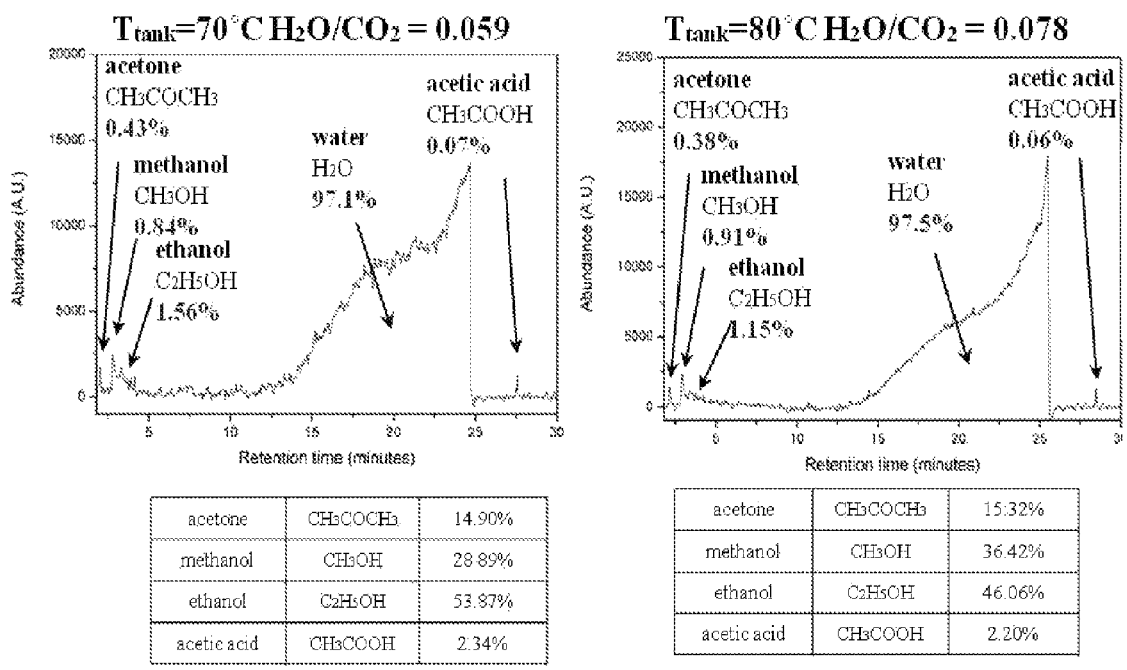
Figure 9C:
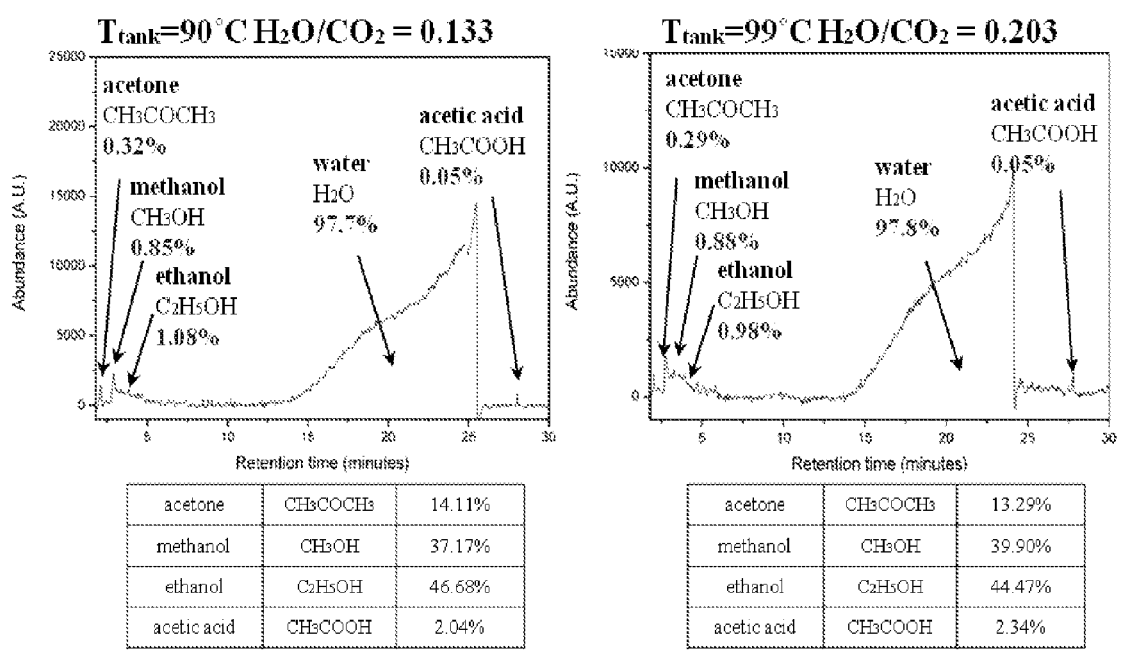

The analysis results of the liquid samples for various reaction temperatures from 50° C. to 99° C. were shown in FIGS. 9A-9C. It was revealed that the total concentration of the organic products collected in the liquid state ranged from 2.2 to 4.3 wt. % (Table 2).

TABLE 2

| Ttank | 50° C. | 60° C. | 70° C. | 80° C. | 90° C. | 99° C. |
|---|---|---|---|---|---|---|
| $W_{collected\ liquid\ products}$ (g)[1] | 1.53 | 1.86 | 2.63 | 3.45 | 7.84 | 10.25 |
| $W_{condensed\ H2O}$ (g)[2] | 0 | 0.04 | 0.52 | 1.47 | 3.83 | 5.41 |
| $H_2O$ concentration in GC-MS ($C_{H2O}$) (%)[3] | 96.4% | 95.7% | 97.1% | 97.5% | 97.7% | 97.8% |
| Liquid products concentration in GC-MS (C* %)[3] | 3.6% | 4.3% | 2.9% | 2.5% | 2.3% | 2.2% |
| Weight of liquid products (Wl) (g)[4] | 0.06 | 0.08 | 0.08 | 0.09 | 0.18 | 0.23 |
| $WH_2O$ in collected liquid products[5] | 1.47 | 1.78 | 2.55 | 3.36 | 7.66 | 10.02 |
| Condensed $H_2O$ in liquid products ($C_{condensed\ H2O}$ %) | 0 | 2.30% | 20.39% | 43.75% | 50.00% | 53.99% |
| Corrected liquid products concentration in GC-MS (C %)[6] | 3.6% | 4.4% | 3.64% | 4.44% | 4.60% | 4.78% |

Figure 9D:
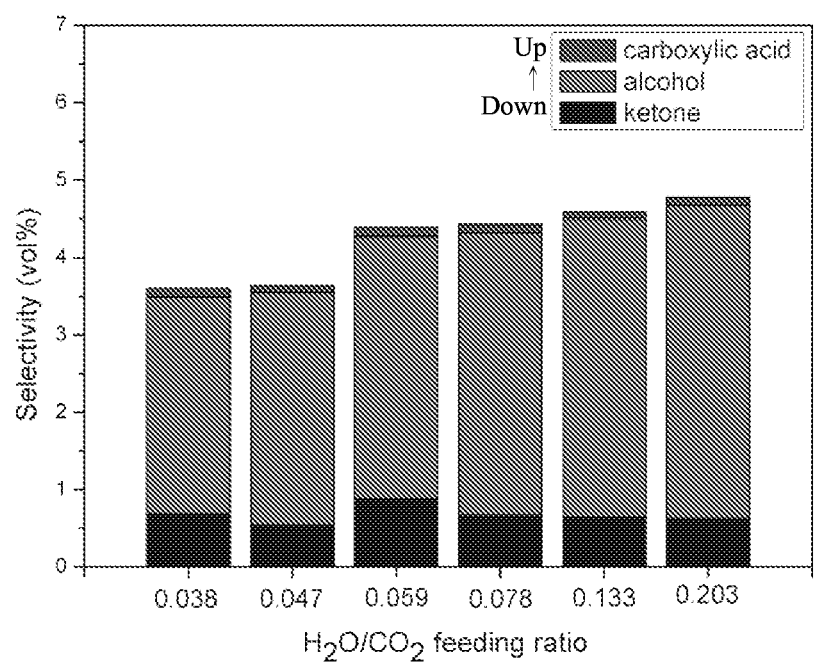
Figure 9E:
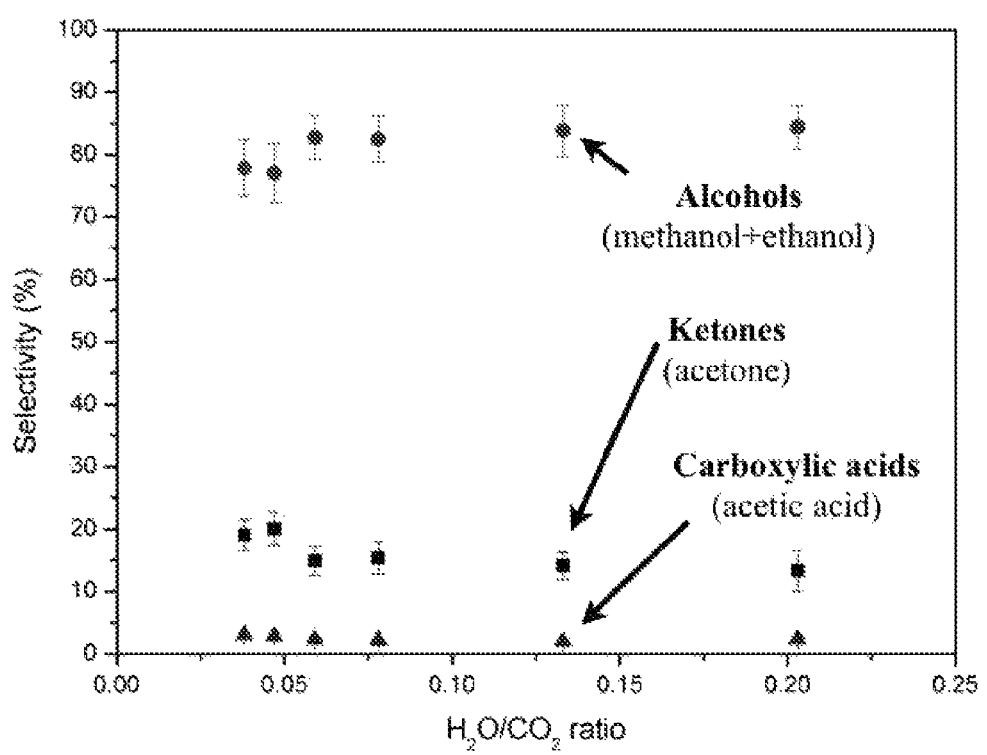

[1]$W_{collected\ liquid\ products}$: The weight of collected APPJ liquid products from cold trap at 4° C.
[2]$W_{condensed\ H2O}$: The weight of condensed $H_2O$ w/o igniting plasma.
[3]obtained from GC-MS results.
[4]$W_{collected\ liquid\ products} \times C^*$ = weight of liquid products (Wl)
[5]$W_{collected\ liquid\ products} \times C_{H2O}$ = weight $H_2O$ in collected liquid products
[6]Corrected liquid products concentration in GC-MS (C %) = C*/$C_{condensed\_H2O}$ The selectivity of liquid products with different $H_2O/CO_2$ ratio was shown in FIG. 9D and FIG. 9E. The total concentration of oxygenates was slightly increased with $H_2O/CO_2$ feeding ratio. More $H_2O$ molecules in the feed produced more hydrogen to hydrogenate $CO_2$, CO and C atoms and form hydrocarbons and oxygenates. The selectivity of alcohols (methanol+ethanol) was much higher than that of ketones (acetone) and carboxylic acids (acetic acid). With the increasing hydrogen concentration in the stream, more H and $C_xH_y$ radicals would be generated and reacted with $CO_2$, CO, O and OH radicals to form oxygenates.

Figure 10:
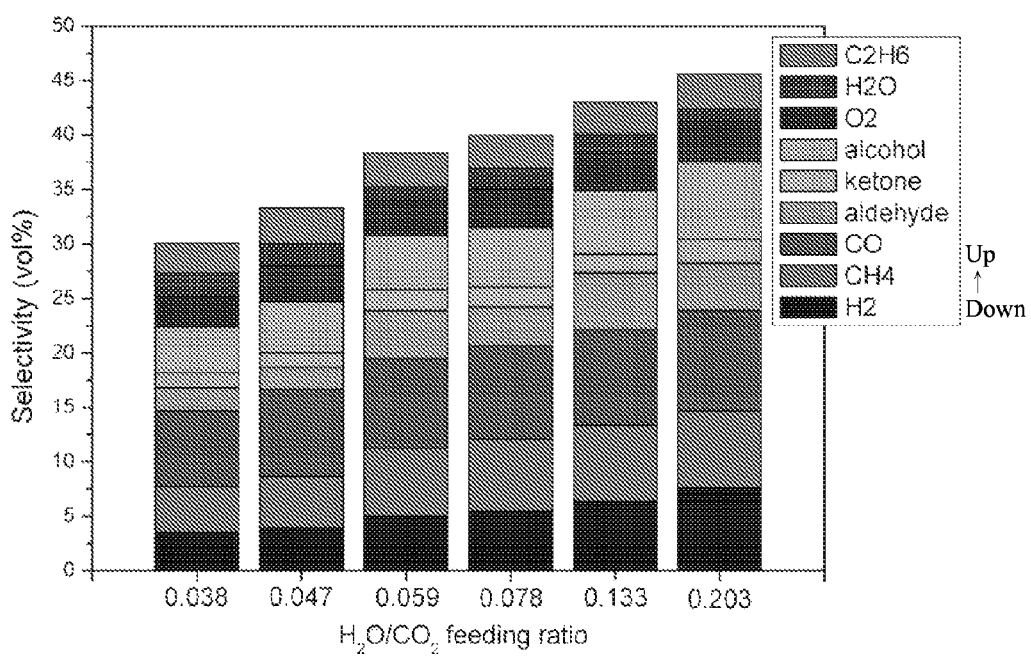
FIG. 10 shows the selectivity, and thus the concentration, of gaseous products with different $H_2O/CO_2$ ratio. The condition of FIG. 10 is as follows: plasma power: 60 W; $CO_2$: 3SLM.

The selectivity of gaseous products with different $H_2O/CO_2$ ratio was shown in FIG. 10. With the increasing hydrogen concentration in the stream, more H and $C_xH_y$ radicals would be generated and reacted with $CO_2$, CO, O and OH radicals to form gaseous products.

Figure 11A:
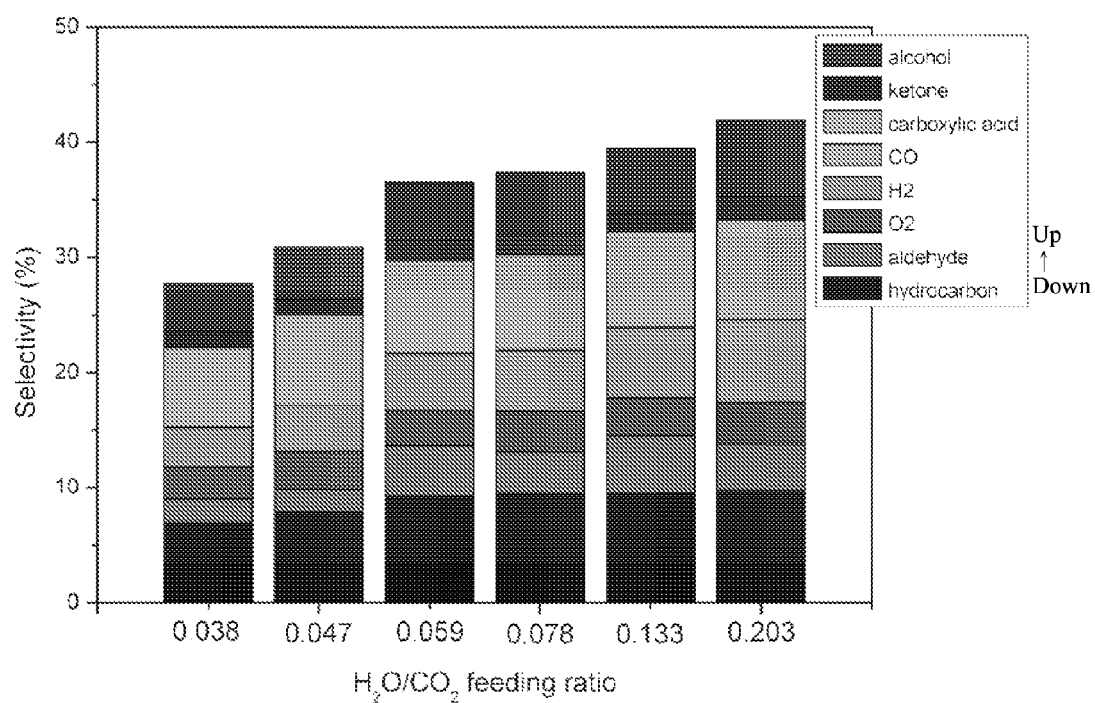
FIGS. 11A-11B shows the total selectivity of $CO_2/H_2O$ atmospheric pressure plasma jet reaction. The plasma power is 60 W. Alcohol: methanol+ethanol; ketone: acetone; carboxylic acid:acetic acid; aldehyde:formaldehyde+acetaldehyde; hydrocarbon:methane+ethane. The total concentration of oxygenates is slightly increased with $H_2O/CO_2$ feeding ratio.
Figure 11B:
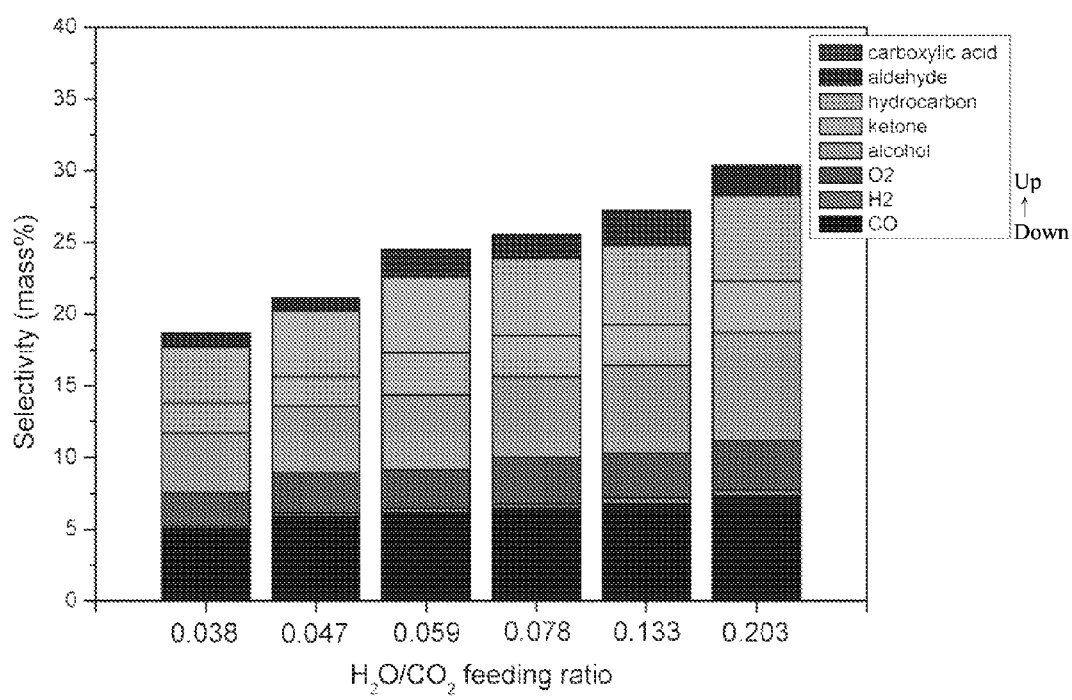

The total concentration of $CO_2/H_2O$ atmospheric pressure plasma jet reaction was shown in FIG. 11. With increasing water in the feed, the concentration of the liquid and gaseous oxygenated products also increased. There was high selectivity in alcohol, hydrocarbon, carbon monoxide and hydrogen gas. Considering the short reaction time, ~7.5 ms, the reaction efficiencies were truly remarkable.

Figure 12:
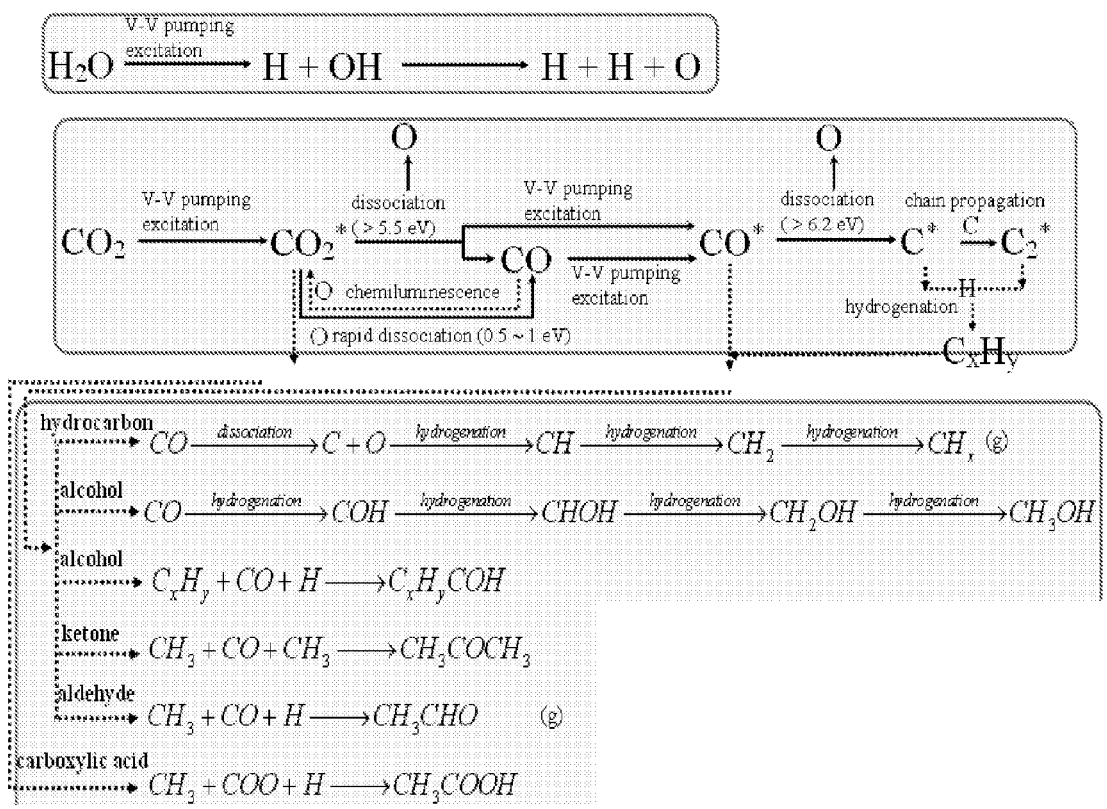
FIG. 12 shows the general scheme of the reaction routes proposed for the conversion reactions in the $CO_2/H_2O$ atmospheric pressure plasma jet reactor.

A general scheme of the reaction routes proposed for the conversion reactions taking place in the $CO_2/H_2O$ atmospheric pressure plasma jet was shown in FIG. 12. Under plasma reactions, where the gas-phase collisions dominate the processes, the $CO_2$ and $H_2O$ molecules dissociated into CO, O, OH and H radicals and then recombined to form oxygenated compounds (alcohols, ketones, aldehydes and carboxylic acids) and light hydrocarbons.

One skilled in the art readily appreciates that the present invention is well adapted to carry out the objects and obtain the ends and advantages mentioned, as well as those inherent therein. The organic products and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of conversion of carbon dioxide into organic products using plasma technology comprising the steps of:
    (a) providing a reaction chamber;
    (b) introducing a counterpart molecule and carbon dioxide into the reaction chamber;
    (c) initiating a plasma in the reaction chamber; and
    (d) converting the carbon dioxide into organic products, wherein the organic products comprise alcohol and acetic acid but do not contain formic acid and formaldehyde,
    and wherein the counterpart molecule consists of water molecule.

2. The method of claim 1, wherein the water molecule is vaporized in the reaction chamber by heating, with plasma assistance or a combination of both.

3. The method of claim 1, wherein the water molecule is vaporized outside the reaction chamber and the vapor is introduced into the reaction chamber directly.

4. The method of claim 1, wherein the water molecule is injected directly or introduced into the reaction chamber by carrier gas.

5. The method of claim 1, wherein the reaction chamber is of glass, metallic materials, ceramics or polymers.

6. The method of claim 1, wherein the chamber pressure is 0.01~760 torr.

7. The method of claim 1, wherein the plasma is low pressure plasma or atmosphere plasma.

8. The method of claim 7, wherein the low pressure plasma is capacitively coupled plasma or inductively coupled plasma.

9. The method of claim 7 wherein the atmosphere plasma is electron beam discharge, corona discharge or dielectric discharge.

10. The method of claim 1, wherein the plasma is microwave plasma, radio frequency (RF) plasma or direct current (DC) plasma.

11. The method of claim 1, wherein the power of the plasma is 0.1~1000 W.

12. The method of claim 1, which is applied in portable device or fixed device.

13. The method of claim 12, wherein the portable device is applied in exhaust pipes of automobiles or motorcycles.

14. The method of claim 12, wherein the fixed device is used in a factory smokestack or household chimney.

* * * * *